(12) United States Patent
Carter et al.

(10) Patent No.: US 8,789,528 B2
(45) Date of Patent: Jul. 29, 2014

(54) PRESSURE SUPPORT METHOD WITH AUTOMATIC COMFORT FEATURE MODIFICATION

(75) Inventors: Duane H. Carter, Irwin, PA (US); Tim Dixon, Trafford, PA (US); Daniel A. Jonczak, Greensburg, PA (US); Zachary Paul, Pittsburgh, PA (US); Benjamin I. Shelly, Pittsburgh, PA (US); Greg Matthews, Pittsburgh, PA (US); Peter D. Hill, Monroeville, PA (US); Andrew DeGuilio, Cheswick, PA (US)

(73) Assignee: Ric Investments, LLC, Wilmington, DE (US)

( * ) Notice: Subject to any disclaimer, the term of this patent is extended or adjusted under 35 U.S.C. 154(b) by 1559 days.

(21) Appl. No.: 12/028,306

(22) Filed: Feb. 8, 2008

(65) Prior Publication Data

US 2008/0216832 A1  Sep. 11, 2008

Related U.S. Application Data

(60) Provisional application No. 60/900,943, filed on Feb. 12, 2007.

(51) Int. Cl.
*A61M 16/00* (2006.01)
*A62B 7/00* (2006.01)
*F16K 31/02* (2006.01)

(52) U.S. Cl.
USPC ........................................... 128/204.21

(58) Field of Classification Search
USPC ............................ 128/204.18, 204.21, 204.23
See application file for complete search history.

(56) References Cited

U.S. PATENT DOCUMENTS

| | | |
|---|---|---|
| 5,148,802 A | 9/1992 | Sanders et al. |
| 5,203,343 A | 4/1993 | Axe et al. |
| 5,313,937 A | 5/1994 | Zdrojkowski |
| 5,433,193 A | 7/1995 | Sanders et al. |
| 5,458,137 A | 10/1995 | Axe et al. |
| 5,632,269 A | 5/1997 | Zdrojkowski |
| 5,645,053 A | 7/1997 | Remmers et al. |
| 5,685,296 A | 11/1997 | Zdrojkowski et al. |
| 5,694,923 A | 12/1997 | Hete et al. |
| 5,701,883 A | 12/1997 | Hete et al. |
| 5,803,065 A | 9/1998 | Zdrojkowski et al. |

(Continued)

FOREIGN PATENT DOCUMENTS

| | | |
|---|---|---|
| EP | 0722747 A2 | 7/1996 |
| EP | 0722747 A3 | 10/1996 |
| WO | WO 2005/065757 | * 7/2005 |

*Primary Examiner* — Kristen Matter
(74) *Attorney, Agent, or Firm* — Michael W. Haas

(57) ABSTRACT

A method of delivering a flow of gas to a patient's airway via a pressure generating system and a patient circuit. A controller receives a treatment set point from an input source and determines an adjusted treatment set point based on the treatment set point and a comfort feature function, which in one embodiment, is not based on a physiological condition of such a patient. In another embodiment, the controller provides a respiratory treatment therapy during a therapy session based on the treatment set point and the comfort feature, which is modified automatically during a therapy session without user intervention based on a comparison of the treatment set point to a treatment set point variable. The controller controls the operation of the pressure generating system based on the adjusted treatment set point or the combination of the treatment set point and the comfort feature.

27 Claims, 4 Drawing Sheets

(56) References Cited

U.S. PATENT DOCUMENTS

| | | |
|---|---|---|
| 6,029,664 A | 2/2000 | Zdrojkowski et al. |
| 6,085,747 A | 7/2000 | Axe et al. |
| 6,123,074 A | 9/2000 | Hete et al. |
| 6,286,508 B1 | 9/2001 | Remmers et al. |
| 6,360,741 B2 | 3/2002 | Truschel |
| 6,532,959 B1 | 3/2003 | Berthon-Jones |
| 6,550,478 B2 | 4/2003 | Remmers et al. |
| 6,584,977 B1 | 7/2003 | Serowski |
| 6,615,831 B1 | 9/2003 | Tuitt et al. |
| 6,626,175 B2 | 9/2003 | Jafari et al. |
| 6,640,806 B2 | 11/2003 | Yurko |
| 6,752,151 B2 | 6/2004 | Hill |
| 6,823,866 B2 | 11/2004 | Jafari et al. |
| 6,920,875 B1 | 7/2005 | Hill et al. |
| 6,920,877 B2 | 7/2005 | Remmers et al. |
| 6,948,497 B2 | 9/2005 | Zdrojkowski et al. |
| 7,000,612 B2 | 2/2006 | Jafari et al. |
| 7,011,091 B2 | 3/2006 | Hill et al. |
| 7,100,607 B2 | 9/2006 | Zdrojkowski et al. |
| 7,134,434 B2 | 11/2006 | Truitt et al. |
| 7,168,429 B2 | 1/2007 | Matthews et al. |
| 2003/0111079 A1 | 6/2003 | Matthews et al. |
| 2003/0121519 A1 | 7/2003 | Estes |
| 2004/0187870 A1 | 9/2004 | Matthews et al. |
| 2004/0211423 A1 * | 10/2004 | Baecke ............ 128/204.23 |
| 2006/0000475 A1 | 1/2006 | Matthews et al. |
| 2006/0070624 A1 | 4/2006 | Kane |
| 2007/0017518 A1 | 1/2007 | Farrugia et al. |
| 2007/0044799 A1 | 3/2007 | Hete et al. |

\* cited by examiner

PRESSURE SUPPORT METHOD WITH AUTOMATIC COMFORT FEATURE MODIFICATION

CROSS-REFERENCE TO RELATED APPLICATIONS

This application claims priority under 35 U.S.C. §119(e) from provisional U.S. patent application No. 60/900,943, filed Feb. 12, 2007, the contents of which are incorporated herein by reference.

BACKGROUND OF THE INVENTION

1. Field of the Invention

The present invention pertains to a method of providing pressure support to treat disordered breathing, and, in particular, to a method that automatically maximizes the comfort of the respiratory treatment therapy delivered to a patient during a therapy session.

2. Description of the Related Art

It is well known that many individuals suffer from disordered breathing during sleep. Examples of sleep disordered breathing include apneas, hypopneas, flow limitations, and Chynes-Stokes respiration. Apneas can be central apneas, which is the result of a loss of a drive to breathe, obstructive apneas, which is the result of a mechanical obstruction of the airway, or mixed (central and obstructive) apneas. Obstructive sleep apnea (OSA), which is believed to be suffered by millions of people through the world, is a condition in which sleep is repeatedly interrupted by an inability to breathe, which occurs due to an obstruction of the airway; typically the upper airway or pharyngeal area. Obstruction of the airway is generally believed to be due, at least in part, to a general relaxation of the muscles that stabilize the upper airway segment, thereby allowing the tissues to collapse the airway.

Those afflicted with OSA experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of OSA include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete obstruction of the airway, it is also known that adverse effects, such as arousals from sleep, can occur where there is only a partial obstruction of the airway. Partial obstruction of the airway typically results in shallow breathing, which is referred to as a hypopnea. Other types of disordered breathing include upper airway resistance syndrome (UARS), which is characterized by the absence of obstructive sleep apnea and oxygen desaturation, yet the patient experience excessive daytime sleepiness, chronic fatigue, and increased respiratory effort during sleep, leading to recurrent arousals, despite the absence of hypopneas or apneas. Still other types of disordered breathing include vibration of the airway, such as vibration of the pharyngeal wall, commonly referred to as snoring. It is also known that snoring can accompany closure of the airway leading to UARS, hypopnea, or apnea.

It is known to treat such disordered breathing by administering a respiratory treatment therapy to the patient. This therapy can take several forms. In one form, the respiratory treatment therapy involves applying a continuous positive air pressure (CPAP) to the patient's airway. This positive pressure effectively "splints" the airway, thereby maintaining an open passage to the lungs. Example of CPAP devices that provide this therapy are the REMstar® family of CPAP devices manufactured by Respironics, Inc. of Pittsburgh, Pa.

In another form, the respiratory treatment therapy involves providing a bi-level positive pressure therapy to the patient. In this treatment therapy, the pressure of fluid delivered to the patient's airway varies or is synchronized with the patient's breathing cycle to maximize the therapeutic effect and comfort to the patient. During inspiration, the patent receives an inspiratory positive airway pressure (IPAP), and during expiration, the patient receives an expiratory positive airway pressure (EPAP) that is lower than the IPAP. An example of a pressure support device that provides "bi-level" pressure support, in which a lower pressure is delivered to that patient during the patient's expiratory phase than during the inspiratory phase, is the BiPAP® family of devices manufactured and distributed by Respironics, Inc. of Pittsburgh, Pa.

It should be noted that bi-level therapies can provide pressure waveforms having a variety of different patterns. For example, the pressure can be delivered in a traditional square wave or in a fashion that more closely mimics the pressure or flow waveform of a healthy human. The term "fluid" used herein refers to any gas, mixture of gasses, or gas with medicine, etc. suitable for delivery to the airway of a human.

It is further known to provide a respiratory treatment therapy in which the pressure provided to the patient is automatically adjusted based on the detected conditions of the patient, such as whether the patient is snoring or experiencing an apnea, hypopnea, or snoring. This respiratory treatment technique is referred to as an auto-titration type of pressure support, because the pressure support device seeks to provide a pressure to the patient that is only as high as necessary to treat the disordered breathing. An example of a device that adjusts the pressure delivered to the patient based on whether or not the patient is snoring is the REMstar® Auto device manufactured and distributed by Respironics, Inc.

Other pressure support systems that offer other modes of providing positive pressure to the patient are also known. For example, a proportional assist ventilation (PAV®) mode of pressure support provides a positive pressure therapy in which the pressure of gas delivered to the patient varies with the patient's breathing effort to increase the comfort to the patient. U.S. Pat. Nos. 5,044,362 and 5,107,830 both to Younes, the contents of which are incorporated herein by reference, teach a pressure support device capable of operating in a PAV mode.

Proportional positive airway pressure (PPAP) devices deliver breathing gas to the patient based on the flow generated by the patient. U.S. Pat. Nos. 5,535,738; 5,794,615; 6,105,575; 6,609,517; and 6,932,084, (collectively referred to as "the PPAP patents") the contents of which are incorporated herein by reference, teach a pressure support device capable of operating in a PPAP mode. Examples a device that adjusts the pressure delivered to the patient based on the patient's respiratory flow is the REMstar® Pro, Plus, or Auto with C-Flex™ or Bi-Flex® devices manufactured and distributed by Respironics, Inc. The term "C-Flex" refers to a device that provides a CPAP respiratory treatment therapy in which the pressure delivered to the patient is reduced in proportion to flow during expiration. The term "Bi-Flex" refers to a device that provides a bi-level respiratory treatment therapy in which either the IPAP or EPAP pressures are further reduced in proportion to flow.

It is also known to provide a combination of such respiratory therapies. For example, a CPAP device with C-Flex can be auto-titrating, such as REMstar® Auto with C-Flex™, so that the CPAP pressure varies during a treatment session based on the monitored condition of the patient. Similarly, a bi-level device with Bi-Flex can be auto-titrating, such as Bi-PAP® Auto with Bi-Flex™, so that the IPAP and EPAP pressures vary during a treatment session based on the monitored condition of the patient. In an auto titrating bi-level device, the difference between IPAP and EPAP, which is referred to as the pressure support (PS), can vary according to the auto-titration algorithm or it can be held constant depending on how the device is configured.

U.S. Pat. No. 6,640,806 discloses a bi-level pressure support system that automatically changes the rise-time and/or fall-time of the pressure transition between IPAP and EPAP. Changing the rise/fall time is done based on the physiological condition of the patient detected by flow, pressure, or other sensors, and may not result in an optimization of the comfort of the overall pressure support therapy.

While auto-titrating devices, bi-level device, devices that include PPAP (C-Flex or Bi-Flex), or any combination of such devices have improved on the basic CPAP device, making the respiratory treatment therapy provided to the patient more comfortable, there is still a need to further improve the comfort of the respiratory treatment therapy even further. The better the comfort, the more likely the patient is to use the therapy.

SUMMARY OF THE INVENTION

Accordingly, it is an object of the present invention to provide a method of providing a respiratory treatment therapy that does not suffer from the disadvantages associated with conventional respiratory therapy techniques. This object is achieved by providing a method that includes generating a pressurized flow of gas; communicating the flow of gas to an airway of a patient; and determining an adjusted treatment set point based on a treatment set point and a comfort feature function. The comfort feature function is not based on a physiological condition of such a patient. The method further includes controlling the flow of gas based on the adjusted treatment set point.

In a further embodiment, this object is achieved by providing a method that includes providing a pressure generating system adapted to generate a pressurized flow of gas; communicating the flow of gas to an airway of a patient; controlling the pressure generating system to provide a respiratory treatment therapy during a therapy session based on a treatment set point and a comfort feature; and adding, deleting, or changing the comfort feature automatically during a therapy session, without user intervention, based on a comparison of the treatment set point to a treatment set point variable.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

A. System Hardware

Figure 1:
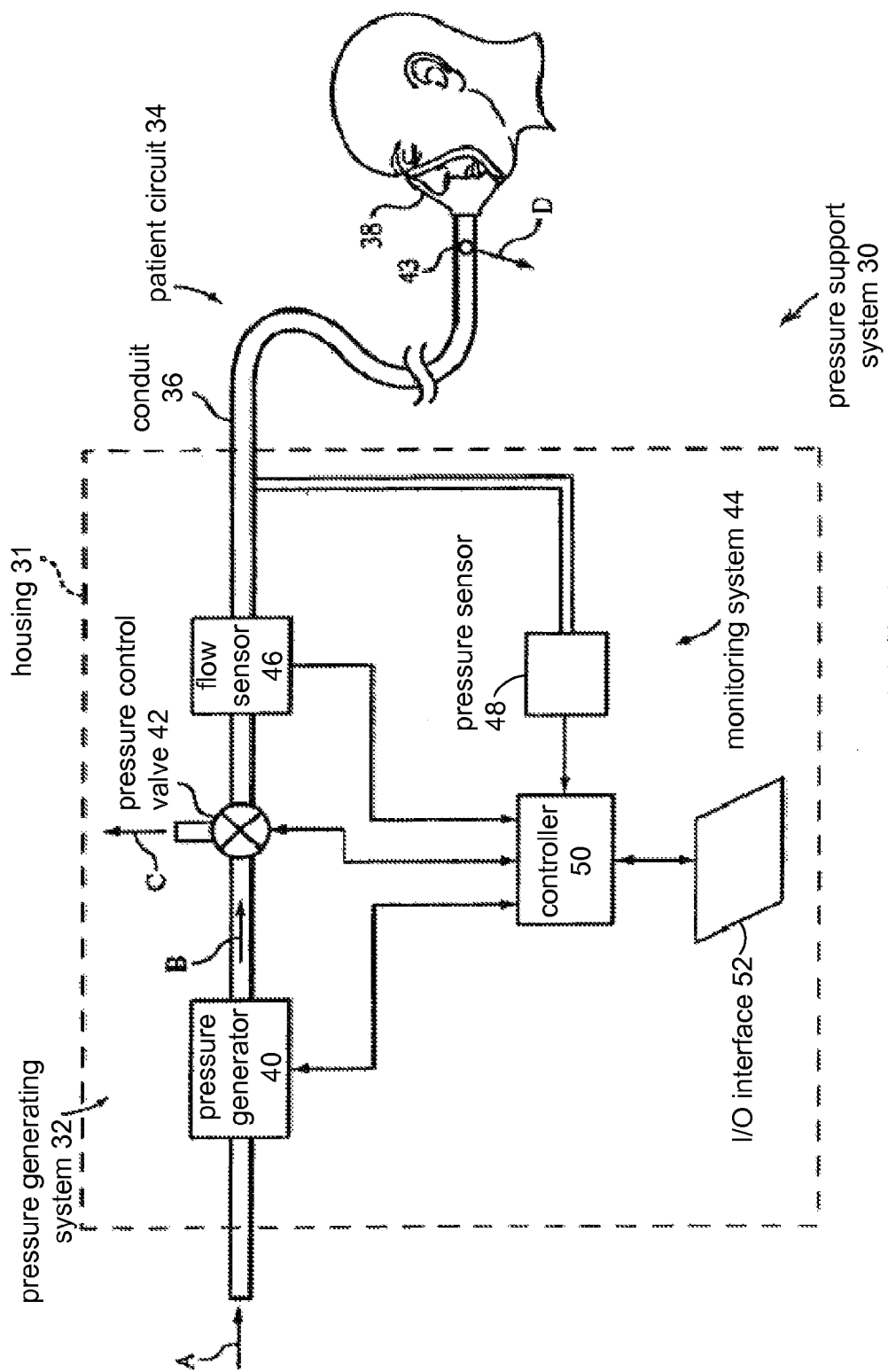
FIG. 1 is a schematic diagram of a pressure support system suitable for implementing the automatic comfort feature modifying technique according to the principles of the present invention.

FIG. 1 schematically illustrates an exemplary embodiment of a pressure support system 30 according to the principles of the present invention. Pressure support system 30 includes a pressure generating system, generally indicated at 32, and a patient circuit 34. Patient circuit 34 includes a conduit 36 and a patient interface device 38. In the illustrated embodiment, pressure generating system 32 includes a pressure generator 40 and a pressure control valve 42 coupled to the outlet of the pressure generator. A housing, indicated by dashed line 31, contains many of the components of the pressure support system.

Pressure generator 40 receives breathing gas from a source of breathing gas, as indicated by arrow A, and outputs the breathing gas, as indicated by arrow B, to patient circuit 34 at a pressure that is greater than atmosphere for delivery to the airway of a patient. In a preferred embodiment of the present invention, pressure generator 40 is a mechanical pressure generator, such as a blower, bellows, or piston, that receives ambient air, for example, at an inlet from the gas source. Pressure control valve 42 controls the pressure of the flow of breathing gas delivered to the patient via the patient circuit by restricting the flow to the patient, by diverting flow from patient circuit 34, as indicated by arrow C, or a combination thereof. Examples of pressure control valves suitable for use in pressure support system are disclosed in U.S. Pat. Nos. 5,694,923; 5,701,883; 6,123,074; 6,615,831; and 7,134,434.

The present invention further contemplates controlling the pressure of the flow of breathing gas delivered to the patient by controlling the operating speed of pressure generator 40, either alone or in combination with valve 42. Of course, valve 42 can be eliminated if the operating speed alone is used to control the pressure of the flow of breathing gas delivered to the patient. Those skilled in the art can appreciate that other techniques for controlling the pressure of the flow of breathing gas delivered to the patient can be implemented in pressure support system 30, either alone or in combination to those discussed above. For example, a flow restricting valve (not shown) can be provided upstream of pressure generator

40 that controls the flow (arrow A) of gas to pressure generator 40, and, hence, the pressure of the flow of gas output for delivery to the patient.

Typically, the source of breathing gas is the ambient atmosphere, where its pressure is subsequently elevated for delivery to the patient by the pressure generating system. It is to be understood, that other sources of breathing gas are contemplated by the present invention, such as oxygen or an oxygen mixture from an oxygen source. It is to be further understood, that the present invention contemplates that pressurized air can be provided to the airway of the patient directly from a tank of pressurized air via the patient circuit without using a pressure generator, such as a blower, bellows or piston, to increase the pressure of the air. Of course, a pressure regulator, such as valve 42 would be required to control the pressure of the gas delivered to the patient. The important feature with respect to the present invention is that pressurized breathing gas is provided in the patient circuit for delivery to the patient, not necessarily the source or manner in which the pressurized breathing gas is generated.

Although not shown in FIG. 1, the present invention also contemplates providing a secondary flow of gas, either alone or in combination with the primary flow of gas (arrow A) from atmosphere. For example, a flow of oxygen from any suitable source can be provided upstream to pressure generator 40 or downstream of the pressure generator in the patient circuit or at the patient interface device to control the fraction of inspired oxygen delivered to the patient. Examples of pressure support systems that include a oxygen delivery module are disclosed in U.S. Pat. Nos. 5,694,923; 5,701,883; and 6,123,074 and in pending U.S. application Ser. No. 11/480, 595 (publication no. US20070044799A1). Of course, gasses or gas mixtures, other than or in addition to oxygen can be provided as the secondary flow of gas. Examples of these include helium, a helium-oxygen mixture (heliox), nitrogen, and a nitrogen-oxygen mixture. Components for introducing other substances, such as medicines, typically in the form of a dry powder or aerosol, can be provided in the pressure generating system of the present invention.

In the illustrated embodiment, conduit 36 in patient circuit 34 has one end coupled to the output of the pressure generator 40 and another end coupled to patient interface device 38. Conduit 36 is any tubing capable of carrying the gas flow from the pressure generator to the airway of the patient. Typically, a distal portion of the conduit 36 relative to pressure generator 40 is flexible to allow for freedom of movement of the patient. It is to be understood that various components may be provided in or coupled to patient circuit 34. For example, a bacteria filter, pressure control valve, flow control valve, sensor, meter, pressure filter, humidifier, and/or heater can be provided in or attached to the patient circuit. Likewise, other components, such as mufflers and filters can be provided at the inlet of pressure generator 40 and at the outlet of valve 42.

Patient interface device 38 in patient circuit 34 is any device suitable for communicating an end of conduit 36 with the airway of the patient. Examples of suitable patient interface devices include a nasal mask, oral mask or mouthpiece, nasal/oral mask, nasal cannula, trachea tube, intubation tube, hood, or full face mask. It is to be understood that this list of suitable interface devices is not intended to be exclusive or exhaustive.

In the single limb patient circuit of the present invention, exhaled gas from the patient typically exits the patient circuit via an exhaust vent 43, as indicated by arrow D. In the illustrated embodiment, exhaust vent 43 is provided on a distal portion of conduit 34. Depending on the tidal volume of the patient and the pressure delivered by pressure support system 30, a small percentage of the exhaled gas may travel back up the conduit into pressure support system 30 and may even be exhausted to atmosphere through the gas inlet of the pressure generator and/or through a pressure control valve 42, if such a valve is being used with the pressure generator.

Typically, exhaust vent 43 is an orifice provided in the conduit that communicates the interior of the conduit with atmosphere, with no active control over the flow of gas from the system. It is to be understood, however, that a wide variety of exhaust devices and configurations are contemplated for use with the pressure generating system of the present invention. For example, U.S. Pat. Nos. 5,685,296 and 6,584,977 disclose an exhalation device and method where the exhalation flow rate through the device remains substantially constant over a range of pressures in the patient circuit. This exhalation device, which is commonly referred to as a plateau exhalation valve or PEV, is suitable for use with the pressure support system of the present invention.

As shown in FIG. 1, pressure support system 30 includes a monitoring system, generally indicated at 44, to monitor the flow and pressure of gas delivered to the patient. In the illustrated embodiment, monitoring system 44 includes a flow sensor 46 that measures a rate at which the breathing gas flows within patient circuit 34. The present invention contemplates that any suitable sensor, such as a conventional pneumatach, can be used for flow sensor 46. It is to be further understood that flow sensor 46 need not be coupled directly to conduit 36. On the contrary, the present invention contemplates the use of any sensor or a plurality of sensors that can quantitatively measure airflow in the patient circuit. For example, flow in the system can be measured at the patient interface device.

The present invention further contemplates that flow can be measured or estimated from monitoring other features of the pressure support system, without the need for a flow sensor. For example, it is known to estimate flow from the motor or piston speed or from torque of the pressure generator used to provide the elevated pressure by pressure generator 40. In short, the present invention contemplates any conventional technique for measuring the flow of gas delivered to the patient.

Monitoring system 44 also includes a pressure sensor 48 that detects the pressure of the gas at the patient. In the illustrated embodiment, pressure sensor 48 is in fluid communication with patient interface device 38 via a conduit 36. In this embodiment, the pressure at the patient is estimated based on the known pressure drop that occurs in tubing 36. It is to be understood, however, that the patient pressure can be measured directly at patient interface device 38 or at other locations along conduit 36.

Pressure support system 30 includes a controller 50, which is preferably a microprocessor capable of implementing a stored algorithm, that receives the monitored variables, typically from flow sensor 46 and pressure sensor 48, and controls pressure generating system 32 based on these signals. Of course, controller 50 includes the necessary memory and processing capability to implement the features of the present invention. In a preferred embodiment of the present invention, controller 50 is an AMTEL AT91M55800 microcontroller that runs stored software written in C programming language.

The present invention further contemplates that pressure support system 30 includes an input/output interface 52 for communicating, information, data and/or instructions and any other communicatable items, collectively referred to as "data", between a user and controller 50. Examples of common input/output interfaces suitable for this purpose include a keypad and display. Other communication techniques, either hard-wired or wireless, are also contemplated by the present invention. For example, the present invention contemplates providing a smart card terminal that enables data to be loaded into controller 50 from the smart card or loaded onto the smart card from the controller. Other exemplary, interface devices and techniques adapted for use with the pressure support system include, but are not limited to, an RS-232 port, CD reader/writer, DVD reader/writer, smart card, RF link, and modem (telephone, cable, or other). In short, any conventional technique for providing, receiving, or exchanging data with controller 50 are contemplated by the present invention as input/output device 52.

Controller 50 also performs conventional leak estimation and respiratory cycle monitoring techniques. The present invention contemplates using any conventional technique for calculating leak $Q_{leak}$, which is the leakage of gas from the pressure support system and includes intentional leaks from the exhaust vent and unintentional leaks from the mask-patient interface, for example. The present invention also contemplates using any conventional technique for taking leak into consideration when determining the patient flow $Q_{patient}$, which is the flow of gas at the airway of the patient, and total flow $Q_{total}$, which is the flow of gas typically measured by flow sensor 46. For example, U.S. Pat. Nos. 5,148,802; 5,313,937; 5,433,193; 5,632,269; 5,803,065; 6,029,664; 6,360,741; 6,626,175; 6,823,866; 6,920,875; 6,948,497; 7,000,612; 7,011,091; and 7,100,607, the contents of each of which are incorporated by reference into the present invention, all teach techniques for detecting and estimating leak and managing the delivery of breathing gas to the patient in the presence of leaks.

The present invention also contemplates using any conventional technique for detecting the inspiratory and expiratory phases of the patient's respiratory cycle. For example, U.S. Pat. Nos. 5,148,802; 5,313,937; 5,433,193; 5,632,269; 5,803,065; 6,029,664; 6,360,741; 6,626,175; 6,823,866; 6,920,875; 6,948,497; 7,000,612; 7,011,091; and 7,100,607, all teach techniques for differentiating between the inspiratory and expiratory phases of a respiratory cycle.

B. System Operation

Figure 2:
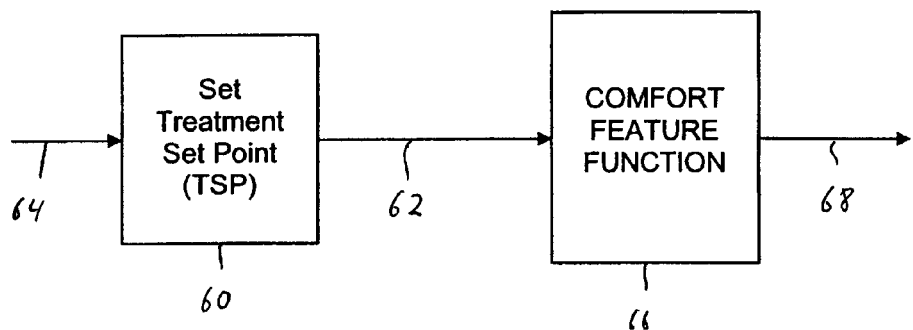
FIG. 2 is a flow chart illustrating the implementation of an exemplary embodiment of the automatic comfort feature modifying technique according to the principles of the present invention.

The operation of pressure support system 30 according to the principles of the present invention will now be described with reference to FIG. 2, which is a schematic diagram of the pressure control process implemented by controller 50 according a simplified version of the present invention. In control step (box) 60, controller 50 determines or is given a treatment set point (TSP), as indicated by arrow 62 output from control step 60. The treatment set point corresponds to a parameter of a respiratory treatment therapy that the controller is attempting to achieve. For example, in a CPAP system, the TSP is the CPAP pressure. In a bi-level system, the TSP is actually two TSPs, which are the IPAP and EPAP levels. In other words, the therapy set point is the value for a controlled parameter or multiple parameters that the controller will attempt to cause the pressure support system to reach during a normal therapy session.

In a conventional CPAP device (without auto-titration), the CPAP pressure is prescribed by a physician and set by the medical device provider. Setting the CPAP pressure, for example, is indicated by input arrow 64. In this example, the set CPAP pressure (e.g., 5 cmH$_2$O) becomes the treatment set point, i.e., no processing need take place in control step 60. Controller 50 in pressure support system 30 controls pressure generating system 32 to deliver a flow of gas to the user at the treatment set point (e.g., 5 cmH$_2$O). The TSP can be changed between or during therapy sessions. For example, a new prescription pressure can be programmed into the CPAP, either at the unit via input/output interface 52 or remotely via a communication link with controller 50.

In a slightly more complicated example, such as a CPAP device with auto-titration, the TSP changes according to the auto-adjusting algorithm implemented by the pressure support system in control step 60. That is, TSP 62 output from processing step 60 corresponds to the pressure level determined by the auto-adjusting algorithm. The input can be the pressure range, i.e., the upper limit $P_{max}$ and/or lower limit $P_{min}$, between which the pressure can vary when implementing the auto-titration algorithm. The present invention contemplates that the auto-adjusting algorithm performed in control step 60 can be any conventional auto-titration technique. The phrase "auto-adjusting" as used herein is intended to encompass auto-titration or auto-titrating modes of pressure support as well as any other mode of setting a treatment set point that is accomplished automatically, i.e., with input from the user. Examples of suitable auto-titration technique are disclosed in U.S. Pat. Nos. 5,203,343; 5,458,137; 6,085,747 all to Axe et al.; 5,645,053; 6,286,508; 6,550,478; 6,920,877 all to Remmers et al.; 6,752,151 to Hill; and 7,168,429 to Matthews et al., the contents of each of which are incorporated herein by reference.

The present invention includes an additional step of implementing a comfort feature function 66, so that the treatment set point includes a comfort feature. In one embodiment, the combination of the treatment set point and the comfort feature is referred to as an adjusted treatment set point and is indicated by output arrow 68 from comfort feature function 66. The controller controls the operation of pressure generating system 32 based on the adjusted treatment set point.

The comfort feature is some form of alteration to the base or underlying respiratory treatment therapy, such as CPAP, that adds to the comfort of the therapy for the user. In an exemplary embodiment, the comfort feature is an expiratory pressure relief, such as C-Flex, that lowers the pressure delivered to the patient during expiration. Please note that the expiratory pressure relief can be based on a monitored parameter, such as flow or pressure, or it can be a predetermined pressure relief, i.e., a pressure reduction that follows a contour or has a shape, duration, and magnitude that is set before the start of expiration.

The comfort feature function is a process, algorithm, paradigm or other implementation scheme that establishes (a) what comfort feature is to be added to, changed, or deleted from the treatment set point, (b) when the comfort feature is to be added, deleted, or changed, and (c) how much (or to what extent) the comfort feature will be added to, changed, or deleted from the treatment set point. The comfort feature function can determine all three of these items or only a subset of these functions, such as only one or two of items (a), (b), or (c). Of course, the comfort feature function can also determine more than just items (a) "what", (b) "when", and (c) "how much" the comfort feature is to be modified to the extent that any other modifications are possible. In an exemplary, but not limiting embodiment, the comfort feature function makes one or more of these determinations based on criteria that is not based on a physiological condition of such a patient.

For purposes of the present application, the process of adding, deleting, or changing an item, such as the comfort feature, is referred to as collectively as "modifying", "modify", "modification" or some variation of the word "modify". Thus, the word "modify" or some variation thereof is used as a shorthand notation for any act of adding, deleting, or changing an item.

Implementing or executing the comfort feature function can be accomplished via a look-up table, a neural network, fuzzy logic, a mathematical formula, or any other process that can receive one or more inputs, act on the input based on a set of rules, formula, or other criteria, and produce and output.

Figure 3:
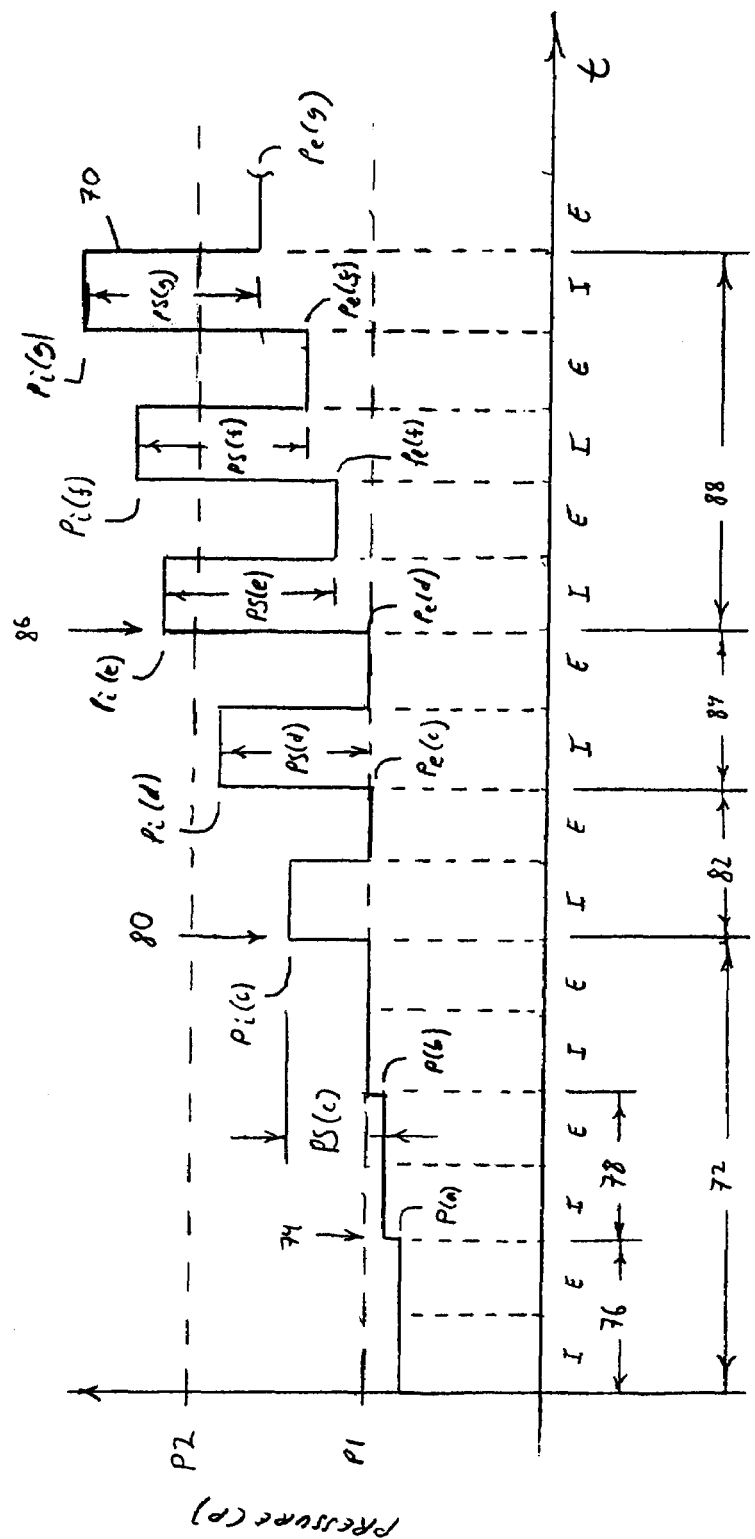
FIG. 3 is a graph illustrating a pressure waveform for a flow of gas provided to a patient according to a first embodiment of the automatic comfort feature modifying technique.

The operation of comfort feature function 66 is perhaps better understood by reviewing an exemplary implementation of the present invention with reference to FIG. 3. This figure shows a pressure waveform 70 provided to the airway of the patient by pressure support system 30 over a plurality of respiratory cycles. Each respiratory cycle includes an inspiratory phase "I" and an expiratory phase "E". In this example, the pressure support system is initially providing a CPAP pressure during period 72. This is illustrated by a constant pressure being delivered during both the inspiratory phases within period 72.

It is to be understood that during this time, an auto-adjusting algorithm is also running in control step 60, so that the CPAP pressure can change. An example of such a change is illustrated by the pressure increase at point 74. The output of the auto-adjusting algorithm (control step 60) corresponds to the treatment set point (TSP). During period 76, the TSP is at pressure level P(a), and during period 78, the TSP is at pressure level P(b). During each processing cycle or prior to the next inspiratory or expiratory phase of the respiratory cycle, the auto-adjusting algorithm determines the treatment set point and controls the pressure generating system to attempt to deliver a pressure to the patient that corresponds to the treatment set point.

In comfort feature function 66, the treatment set point, as determined by the auto-adjusting algorithm, is being compared to a treatment set point variable. In this embodiment, the treatment set point variable is preset pressure P1. This comparison can be done periodically or during every processing cycle of the controller. As long as the treatment set point is at or below the treatment set point variable (P1 in this example), no comfort features or changes to the existing comfort feature takes place. Thus, as long as TSP is ≤P1, the pressure support system functions as a conventional CPAP auto-titration system.

If, however, the treatment set point is greater than the treatment set point variable, the comfort feature function of present invention adds a comfort feature to the respiratory treatment therapy being delivered to the patient. In the illustrated embodiment, the treatment set point Pi(c) to be delivered the patient, as determined by the auto-adjusting algorithm, for the inspiratory phase that begins a point 80 is greater than the treatment set point variable P1. Such increases in the treatment set point can occur, for example, if the system detects that the patient is experiencing (or is about to experience) snoring, flow limitations, apneas, hypopneas, CSR, or other breathing disorders. When the TSP, which at point 80 is Pi(c), is greater than the treatment set point variable, which is set as P1, the comfort feature is added. In this illustrated embodiment, the comfort feature added to the pressure waveform is to provide expiratory pressure relief to the patient, rather than maintain a constant pressure during both inspiration and expiration. Thus, an IPAP at the treatment set point Pi(c) is delivered during inspiration, and an EPAP Pe(c) is delivered during expiration. As noted above, the difference between Pi(c) and Pe(c), i.e., the difference between IPAP and EPAP, is referred to as the pressure support level (PS). Thus, IPAP−EPAP=PS.

So long as the treatment set point remains below a second pressure threshold, which in this illustrated exemplary embodiment is pressure P2, the EPAP level is set to the treatment set point variable level P1, so that EPAP=P1. In other words, as long as the TSP is greater than P1 and less than P2, the pressure support PS can vary due to changes in the IPAP level based on the TSP, but the EPAP level remains fixed to the treatment set point variable level P1. This set of rules, is contained in and implemented by comfort feature function 66. Thus, during period 82, the pressure support level is PS(c), and during period 84, the PS=PS(d), which is greater than PS(c).

However, at point 86, the treatment set point becomes greater than the second pressure threshold P2. At this point, the IPAP pressure Pi(e) still corresponds to the TSP, but the EPAP pressure is no longer fixed at P1. Instead, at this point, the pressure support PS level does not vary, but is locked to a fixed amount, so that the EPAP level is always less than the IPAP level by a fixed amount. As long as the TSP remains above the second pressure threshold P2, which is the case during period 88, the pressure support remains fixed and the EPAP pressure tracks with the IPAP pressure. Thus, PS(e)= PS(f)=PS(g). If the TSP falls below the second pressure threshold P2, EPAP is set to P1 and the PS level is allowed to vary. Similarly, is the TSP falls below the treatment set point variable level P1, the PS level is set to zero (0), so that IPAP=EPAP, and the patient is again receiving a CPAP, rather than a bi-level therapy.

It can be appreciated from the discussion above, that the pressure support system of the present invention provides a comfort feature to the respiratory treatment therapy being delivered to the patient. In the above-described embodiment, the comfort feature is the addition or change in the pressure support PS level. Its change, addition, or deletion, i.e., modification, is based on a comparison of the treatment set point, which varies based on the output of an auto-adjusting algorithm in control set 60, with a treatment set point variable, e.g., pressure P1 and/or P2, which was set in advance.

Figure 4:
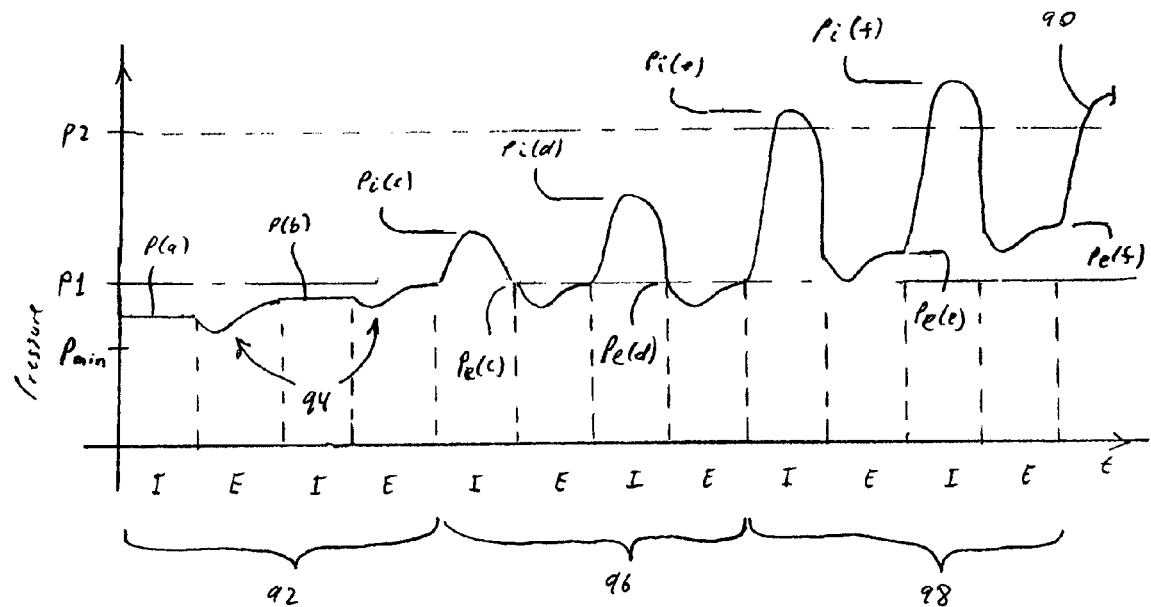
FIG. 4 is a graph illustrating a pressure waveform for a flow of gas provided to a patient according to a second embodiment of the automatic comfort feature modifying technique.

FIG. 4 is a graph that is similar to that of FIG. 3 in that it shows a pressure waveform 90 provided to the airway of the patient by pressure support system 30 over a plurality of respiratory cycles. In FIG. 4, a CPAP therapy with C-Flex already added is being administered during period 92, which is the period when the TSP is below treatment set point variable level P1. That is, a C-Flex type of expiratory pressure relief, as indicated by arrow 94, is being provided during the expiratory phase of the respiratory cycle.

During period 96, in which the TSP is greater than treatment set point variable level P1, the pressure support PS is increased from zero, i.e., is made greater than zero, so that the respiratory treatment therapy switches from a CPAP with C-Flex respiratory treatment therapy, to a bi-level respiratory treatment therapy with expiratory pressure relief. During period 96, i.e., P1<TSP<P2, the PS level can vary, with the EPAP level being fixed to the treatment set point variable level P1. The expiratory pressure relief is still provided to the EPAP level so that the actual pressure delivered falls below the set EPAP level of Pe(c) or Pe(d), for example. During period 98, in which the TSP is greater than second treatment set point variable P2, the PS level is fixed. Thus, the EPAP level can rise or track the changes in the IPAP level.

Pressure waveform 90 is also smoother than that of FIG. 3, i.e., the rise rate from EPAP to IPAP and fall rate from IPAP to EPAP is more gradual. This also is believed to contribute to patient comfort. In addition to an expiratory comfort relief, such as that disclosed in the PPAP patents, pressure relief can also be provided during the inspiratory phase, which is referred to above as Bi-Flex.

The above-described embodiments represent only two examples of the operation of the pressure support system according to the principles of the present invention in which a comfort feature is added, deleted, or changed according to a comfort feature function. It is to be understood that the present invention contemplates a myriad of variations of this basic operating routine. The following discussion, which is provided with reference to FIGS. 1 and 3-5, highlight some of these possible variations.

Figure 5:
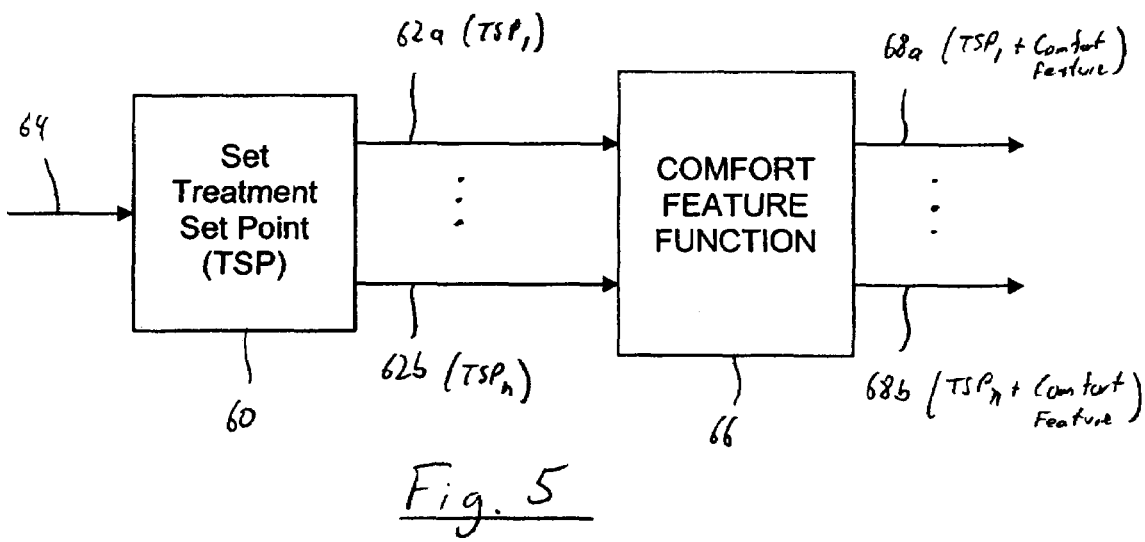
FIG. 5 is a flow chart illustrating the implementation of a further exemplary embodiment of the automatic comfort technique modifying technique according to the principles of the present invention.

As shown in FIG. 5, there may be more than one treatment set point 62a and 62b provided to the comfort feature function from control step 60. For example, $TSP_1$ can be an IPAP set point and $TSP_2$ can be an EPAP setting. Each treatment set point can be acted upon differently depending on the algorithm implemented by comfort feature function step 66. For example, a PPAP type of pressure relieve can be provided to $TSP_1$ and not to $TSP_2$, or vice versa. The amount of the comfort feature can also be different for each of the treatment set points. That is, different comfort feature schedules, routines, algorithms, rules, etc. may be applied to different treatment set points. Consequently, there can also be multiple adjusted treatment set points 68a and 68b that are used to control the operation of the pressure generating system.

In the embodiments discussed above, the treatment set point corresponds to a pressure level, such as a CPAP level, an IPAP level, an EPAP level, a pressure support level, a peak pressure, a PEEP level, or an average pressure. This is perhaps best suited for situations when the pressure generating system is delivering the flow of gas based on pressure. However, the present invention also contemplates that the comfort feature+ TSP feature of the present invention need not be limited to pressure based respiratory treatment therapies and devices that provide such therapies. For example, it is known to deliver gas to a patient based on flow, volume, or duration. In a flow-based system, the treatment set point corresponds to the flow related parameter that the system is attempting to achieve, such as peak volume, a peak flow, an average volume, tidal volume, or an average flow. Similarly, in a system that delivers a flow of gas based on time, the treatment set point corresponds to the time related parameter that the system is attempting to achieve, such as an inspiration duration, an expiration duration, or a breath rate.

There can be many reasons for adding, deleting, or changing, (collectively referred to as "modifying") the comfort feature associated with a given TSP. For example, the present invention contemplates modifying the comfort feature based on time, such as the time spent in a certain therapy mode, the time elapsed since the pressure support system was turn-on or activated, the time elapsed since the last comfort feature modification.

In the embodiment discussed above, the comfort feature is modified based on preset pressures, namely the first and second treatment set point variables P1 and P2. The present invention contemplates that only one such variable can be used, or using more than one such variable. The present invention further contemplates modifying the comfort feature as a function of or based on the flow or volume of gas delivered to or received from the user. For example, if the flow of gas provided to the patient is relatively high, there will be less of a need to modify the comfort feature than when the flow rate is low. The present invention further contemplates modifying the comfort feature as a function of a setting of the pressure support system, such as backup breath rate setpoint.

In addition, the present invention contemplates that the treatment set point variable or variables that are used to determine whether to modify the comfort feature can themselves be subject to modification. For example, a pressure based treatment set point variable, such as P1 or P2, can be changed based on the rate or volume of the flow of gas. A flow based treatment set point variable can change based on the pressure of the flow of gas. In short, the treatment set point variable or variable used by the comfort feature function to determine when and how to modify the comfort feature associated with a given treatment set point need not be static, but can be dynamically changing during the operation of the pressure support system or over time.

The present invention contemplates modifying the comfort feature as a function of a monitored condition of the patient, such as awake/asleep state, sleep stage (1-4, REM), the presence of full or partial airway obstruction (e.g., apnea, hypopnea, snoring, flow limitations, respiratory event related arousals (RERAs), airway resistance, forced oscillation, etc.), the respiratory drive and central sleep apnea, blood gas concentration, oxygen saturation ($SaO_2$), carbon dioxide or oxygen content in exhaled breath, patient health or illness state (such as degree of CHF, asthma, cold, flu, etc.), the activity of the patient, or any combination thereof.

The present invention also contemplates modifying the comfort feature as a function of the hardware used by the pressure support system. For example, a different comfort feature modification can be made depending on whether or not a humidifier is being used in the patient circuit, the type of patient interface device being used, whether the patient is receiving supplemental oxygen, medicine, or other secondary treatments. The modification of the comfort feature can also be on a patient circuit change, whether that change is detected automatically or input into the pressure support system. Examples of patient circuit changes include a hose change or occlusion and mask (patient interface) change or occlusion.

The present invention contemplates modifying the comfort feature as a function of the location of the pressure support system, e.g. altitude, or the ambient conditions of the device, e.g. atmospheric or barometric pressure, temperature, oxygen concentration, relative or absolute humidity, etc.). Modifying the comfort feature could also be done based on an internal device parameter that is unrelated to patient therapy or to a measure of the device used as a surrogate to a physiological measure (e.g. motor current as a surrogate for patient airflow, etc.).

The present invention contemplates modifying the comfort feature as a function of one or more of the following, considered either alone or in any combination:

a) pressure,
b) flow or volume,
c) time,
d) device settings (CPAP, IPAP, EPAP, pressure support, backup breath rate, time of inspiration, humidification setting, target volume, target flow, peak volume, peak flow, peak pressure, average volume, average flow, average pressure),
e) hardware associated with the pressure support system, (e.g., patient circuit type, patient interface type, humidifier type, filter type, sensor type, supplemental oxygen, etc.),
f) environmental conditions (altitude, humidity, temperature, etc.),
g) the condition of the patient (awake/asleep state, sleep stage, airway patency, respiratory drive, patient health, oxygen saturation ($SaO_2$) levels, activity levels, etc.), and
h) usage of the pressure generating system (compliance).

The present invention contemplates that the addition, deletion, or change in the comfort feature can take place gradually, over the course of several therapy sessions, or even over the course of months or years. This may be best suited to situations where the user's needs or comfort desires change over time. Conversely, the addition, deletion, or change in the comfort feature to be associated with a treatment set point can also happen rapidly and may take place multiple times, such as over the course of several minutes or hours, over the course of several breaths, or even on a breath-by-breath basis.

The present invention contemplates that modifying the comfort feature or the need to modify a comfort feature can be reported to someone in some manner. For example, it can be reported to the to the patient, the clinician, or to another therapy monitoring device, through alarms, removable media, led/screen interface, wired, and wireless communication, email, and any other of alerts or alarms.

The need to modify the comfort feature can be determined by a physiologic/diagnostic monitor that is separate from, or independent of the parameters already being monitored by the pressure support system. The clinical decision as to when and how the comfort feature should be modified can be made automatically, by decision algorithms within the therapy device, diagnostic device, or a combination of both, and may include physiologic parameter data from either the therapy or diagnostic systems. The location of the physiologic parameter analysis and clinical decision algorithms may also be remote from the pressure support system, and the clinical decision may involve clinician input. The present invention also envisions that the physiologic/diagnostic monitoring can be performing its evaluation continuously or intermittently during any time interval, including times whether the patient is not receiving the respiratory treatment therapy from the pressure support system.

The present invention contemplates that modifying the comfort feature can occur as a result of tertiary parameters, such as compliance, which is the measured usage of the pressure support system by the patient. For example, the present invention contemplates modifying the comfort feature in a dynamic fashion to attempt to achieve the combination of TSP and comfort feature that maximizes the user's compliance with the pressure support therapy. For example, several combinations of C-Flex, C-Flex levels, and/or bi-level pressure settings can be tried as the comfort feature. Compliance outcomes can then be determined after analyzing the compliance data gathered from one or more therapy sessions. The optimal comfort feature then be selected, and used going forward.

The present invention also contemplates adding more than one comfort feature to a treatment set point. Also, a wide variety of items can be targeted as the comfort feature. For example, comfort features that can be added, deleted, or changed include changes associated with pressure (such as adding, removing or changing a variable associate with PPAP, PAV, rise-rate, and/or pressure support) and changes associated with flow (such as flow rate/volume changes).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of providing a respiratory treatment therapy to a patient, comprising:
   generating a pressurized flow of gas;
   communicating the pressurized flow of gas to an airway of a patient;
   receiving a treatment set point in accordance with a therapy mode, wherein the therapy mode spans at least one or more respiratory cycles,
   determining an adjusted treatment set point based on the received treatment set point and a comfort feature function, wherein activation of the comfort feature function results in the adjusted treatment set point being implemented in place of the received treatment set point, wherein activation of the comfort feature function is based on one or more of time spent in the therapy mode, and/or time elapsed since activation of the pressurized flow of gas; and
   controlling the flow of gas based on the adjusted treatment set point for at least one complete respiratory cycle responsive to the comfort feature function being activated.

2. The method of claim 1, wherein determining the adjusted treatment set point is done a plurality of time during the at least one complete respiratory cycle or a previous respiratory cycle.

3. The method of claim 1, wherein the treatment set point corresponds to a CPAP level, an IPAP level, an EPAP level, a pressure support level, a peak pressure, a peak volume, a peak flow, a PEEP level, an average pressure, an average volume, an average flow, an inspiration duration, or an expiration duration.

4. The method of claim 1, further comprising the step of changing the treatment set point during a therapy session manually or by means of an auto-adjusting algorithm.

5. The method of claim 1, wherein activation of the comfort feature function is further based on one or more of ambient humidity and/or altitude associated with communicating the pressurized flow of gas.

6. The method of claim 1, wherein activation of the comfort feature function based on time spent in the therapy mode is based on one or more hours of time spent in the therapy mode.

7. The method of claim 1, wherein the comfort feature function introduces a comfort feature to the treatment set point to determine the adjusted treatment set point, wherein the comfort feature includes an adjustment in at least one of: pressure, peak pressure, flow, peak flow, volume, peak volume, or rise rate from the received treatment set point.

8. The method of claim 1, wherein activation of the comfort feature function is performed gradually over a course of one or more months of respiratory therapy.

9. The method of claim 1, wherein the therapy mode corresponds to a bi-level pressure support, wherein receiving a treatment set point includes receiving a plurality of treatment set points, wherein determining the adjusted treatment set point includes determining a plurality of adjusted treatment set points based on the received plurality of treatment set points from one or more input sources and one or more comfort feature functions, wherein individual activations of the one or more comfort feature functions correspond to individual ones of the plurality of adjusted treatment set points being different from the corresponding individual ones of the received plurality of treatment set points, wherein individual activations of the one or more comfort feature functions are based on one or more of time spent in the therapy mode, and/or time elapsed since activation of the pressurized flow of gas.

10. A method of providing a respiratory treatment therapy to a patient, comprising:
   generating a pressurized flow of gas with a pressure generating system;
   communicating the pressurized flow of gas to an airway of a patient;

receiving a treatment set point in accordance with a therapy mode, wherein the therapy mode spans at least one or more respiratory cycles; and controlling the pressure generating system to provide the therapy mode during a therapy session based on the received treatment set point and a comfort feature, wherein the comfort feature is added, deleted, or changed automatically during a therapy session without user intervention, wherein activation of the comfort feature results in a reduction of a pressure of the pressurized flow of gas being implemented in place of the received treatment set point in at least one phase of respiration, wherein activation of the comfort feature is based on one or more of ambient humidity and/or altitude associated with the pressure generating system, and wherein controlling the pressure generating system is performed for at least one complete respiratory cycle responsive to the comfort feature being activated.

11. The method of claim 10, wherein adding, deleting, or changing the comfort feature is done a plurality of times during the at least one complete respiratory cycle or a previous respiratory cycle.

12. The method of claim 10, wherein the treatment set point corresponds to a CPAP level, an IPAP level, an EPAP level, a pressure support level, a peak pressure, a peak volume, a peak flow, a PEEP level, an average pressure, an average volume, an average flow, an inspiration duration, or an expiration duration.

13. The method of claim 10, further comprising the step of changing the treatment set point during a therapy session manually or by means of an auto-adjusting algorithm.

14. The method of claim 10, wherein activation of the comfort feature is performed gradually over a course of one or more months of respiratory therapy.

15. The method of claim 10, wherein the comfort features includes an adjustment in at least one of: pressure, peak pressure, flow, peak flow, volume, peak volume, or rise rate from the received treatment set point.

16. The method of claim 10, wherein activation of the comfort feature is further based on a humidifier being associated with the pressure support system.

17. The method of claim 10, wherein activation of the comfort feature is further based on one or more of time spent in the therapy mode, and/or time elapsed since activation of the pressurized flow of gas.

18. The method of claim 10, wherein activation of the comfort feature is further based on a predetermined period that has elapsed since a previous activation of the comfort feature such that subsequent activations of the comfort feature are at least the predetermined period apart, wherein the predetermined period is at least one or more hours.

19. A method of providing a respiratory treatment therapy to a patient, comprising:

generating a pressurized flow of gas with a pressure generating system;

communicating the pressurized flow of gas to an airway of a patient;

receiving a treatment set point in accordance with a therapy mode, wherein the therapy mode spans at least one or more respiratory cycles; and controlling the pressure generating system to provide the therapy mode during a therapy session based on the received treatment set point and a comfort feature, wherein the comfort feature is added, deleted, or changed automatically during a therapy session without user intervention, wherein activation of the comfort feature results in a reduction of a pressure of the pressurized flow of gas being implemented in place of the received treatment set point in at least one phase of respiration, wherein the comfort feature is based on a comfort feature function, wherein activation of the comfort feature function is based on one or more of patient circuit type, patient interface type, and/or filter type associated with the pressure generating system, and wherein controlling the pressure generating system is performed for at least one complete respiratory cycle responsive to the comfort feature function being activated.

20. The method of claim 19, wherein adding, deleting, or changing the comfort feature is done a plurality of times during the at least one complete respiratory cycle or a previous respiratory cycle.

21. The method of claim 19, wherein the treatment set point corresponds to CPAP level, an IPAP level, an EPAP level, a pressure support level, a peak pressure, a peak volume, a peak flow, a PEEP level, an average pressure, an average volume, an average flow, an inspiration duration, or an expiration duration.

22. The method of claim 19, further comprising the step of changing the treatment set point during a therapy session manually or by means of an auto-adjusting algorithm.

23. The method of claim 19, wherein activation of the comfort feature function is furthermore based on one or more of ambient humidity and/or altitude associated with communicating the pressurized flow of gas.

24. The method of claim 19, wherein activation of the comfort feature is performed gradually over a course of one or more months of respiratory therapy.

25. The method of claim 19, wherein the comfort feature is an adjustment in at least one of: pressure, peak pressure, flow, peak flow, volume, peak volume, or rise rate from the received treatment set point.

26. The method of claim 19, wherein activation of the comfort feature is further based on the one or more of time spent in the therapy mode, and/or time elapsed since communicating the pressurized flow of gas.

27. The method of claim 26, wherein activation of the comfort feature is based on time spent in the therapy mode is based on one or more hours of time spent in the therapy mode.

* * * * *